United States Patent
Watanabe et al.

(10) Patent No.: US 10,687,980 B2
(45) Date of Patent: *Jun. 23, 2020

(54) SYSTEM AND METHOD OF IRIS-PUPIL CONTRAST ENHANCEMENT

(71) Applicant: AMO Development, LLC, Santa Ana, CA (US)

(72) Inventors: Keith Watanabe, Irvine, CA (US); Jesse Buck, San Marcos, CA (US)

(73) Assignee: AMO Development, LLC, Santa Ana, CA (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/236,220

(22) Filed: Aug. 12, 2016

(65) Prior Publication Data
US 2016/0346128 A1 Dec. 1, 2016

Related U.S. Application Data

(62) Division of application No. 12/416,346, filed on Apr. 1, 2009, now Pat. No. 9,421,131.

(Continued)

(51) Int. Cl.
*A61F 9/008* (2006.01)
*A61B 18/18* (2006.01)
(Continued)

(52) U.S. Cl.
CPC .......... *A61F 9/00827* (2013.01); *A61B 34/10* (2016.02); *A61F 9/008* (2013.01);
(Continued)

(58) Field of Classification Search
CPC .................. A61F 9/008; A61F 9/00827; A61F 2009/00844; A61F 2009/00872;
(Continued)

(56) References Cited

U.S. PATENT DOCUMENTS

| | | | |
|---|---|---|---|
| 4,677,477 A * | 6/1987 | Plut | H04N 5/32 348/E5.086 |
| 4,764,930 A | 8/1988 | Bille et al. | |

(Continued)

FOREIGN PATENT DOCUMENTS

| | | |
|---|---|---|
| EP | 1080706 A1 | 3/2001 |
| EP | 1324259 A1 | 7/2003 |

(Continued)

OTHER PUBLICATIONS

Gonzalez et al., "Digital Image Processing," pp. 120-143, 2007.

(Continued)

*Primary Examiner* — Allen Porter
(74) *Attorney, Agent, or Firm* — Johnson & Johnson Surgical Vision, Inc.

(57) ABSTRACT

System and method of photoaltering a region of an eye using an enhanced contrast between the iris and the pupil of the imaged eye. The system includes a laser assembly outputting a pulsed laser beam, a user interface displaying one of a first digital image of the eye and a second digital image of the eye, and a controller coupled to the laser assembly and the user interface. The first digital image has a first contrast between the pupil and the iris, and the second digital image has a second contrast between the pupil and the iris. The controller selectively increases the first contrast between the pupil and the iris to the second contrast between the pupil and the iris and directs the pulsed laser beam to the region of the eye based on one of the first and second digital images.

18 Claims, 5 Drawing Sheets

Related U.S. Application Data (60) Provisional application No. 61/041,547, filed on Apr. 1, 2008.

(51) Int. Cl.
*A61B 34/10* (2016.01)
*A61B 3/10* (2006.01)

(52) U.S. Cl.
CPC ........... *A61B 3/10* (2013.01); *A61B 2034/107* (2016.02); *A61F 2009/00844* (2013.01); *A61F 2009/00872* (2013.01); *A61F 2009/00897* (2013.01)

(58) Field of Classification Search
CPC .............. A61F 2009/00897; A61F 9/00; A61F 9/00802; A61F 2009/00846; A61F 2009/00878; A61B 34/10; A61B 2034/107; A61B 3/10; A61B 3/1025; A61B 3/14; A61B 18/20
See application file for complete search history.

(56) References Cited

U.S. PATENT DOCUMENTS

| | | | |
|---|---|---|---|
| 5,098,426 A | 3/1992 | Sklar et al. | |
| 5,473,373 A | 12/1995 | Hwung et al. | |
| 5,549,632 A | 8/1996 | Lai | |
| 5,993,438 A | 11/1999 | Juhasz et al. | |
| 5,993,439 A | 11/1999 | Costello et al. | |
| 6,099,522 A | 8/2000 | Knopp et al. | |
| 6,120,461 A | 9/2000 | Smyth | |
| 6,280,436 B1 | 8/2001 | Freeman et al. | |
| RE37,585 E | 3/2002 | Mourou et al. | |
| 6,630,938 B1 | 10/2003 | Nanni | |
| 6,648,877 B1 | 11/2003 | Juhasz et al. | |
| 7,146,983 B1 | 12/2006 | Hohla et al. | |
| 7,431,457 B2 * | 10/2008 | Chernyak | A61B 3/1015 351/205 |
| 7,448,753 B1 | 11/2008 | Chinnock | |
| 8,262,646 B2 * | 9/2012 | Frey | A61F 9/008 606/4 |
| 2002/0133144 A1 | 9/2002 | Chan et al. | |
| 2003/0009156 A1 | 1/2003 | Levine | |
| 2003/0151720 A1 | 8/2003 | Chernyak et al. | |
| 2004/0054359 A1 | 3/2004 | Ruiz et al. | |
| 2004/0243111 A1 | 12/2004 | Bendett et al. | |
| 2005/0119642 A1 | 6/2005 | Grecu et al. | |
| 2005/0206645 A1 | 9/2005 | Hancock | |
| 2005/0277913 A1 | 12/2005 | McCary | |
| 2007/0225690 A1 | 9/2007 | Sekiguchi et al. | |
| 2008/0009840 A1 | 1/2008 | Chernyak | |
| 2008/0066135 A1 | 3/2008 | Brodersen et al. | |

FOREIGN PATENT DOCUMENTS

| | | |
|---|---|---|
| WO | 06060323 A1 | 6/2006 |
| WO | 2008066135 A1 | 6/2008 |

OTHER PUBLICATIONS

Gonzalez R C. et al., "Digital Image Processing, Chapter 3—Image Enhancement in the Spatial Domain," Digital Image Processing, pp. 78-84, 2002, Prentice Hall, Upper Saddle River, NJ.

International Preliminary Report on Patentability and Written Opinion for Application No. PCT/US09/039186, dated Oct. 5, 2010, 9 pages.

International Preliminary Report on Patentability and Written Opinion for Application No. PCT/US09/039191, dated Oct. 5, 2010, 8 pages.

International Search Report for Application No. PCT/US09/039186, dated Jul. 17, 2009, 4 pages.

International Search Report for Application No. PCT/US09/039191, dated Jul. 6, 2009, 3 pages.

Patent Examination Report dated Jan. 21, 2013 for Australian Patent Application No. 2009231687 filed Apr. 1, 2008.

* cited by examiner

SYSTEM AND METHOD OF IRIS-PUPIL CONTRAST ENHANCEMENT

CROSS-REFERENCE TO RELATED APPLICATION

This application is a divisional of and claims priority to U.S. application Ser. No. 12/416,346, filed Apr. 1, 2009, which claims the benefit of U.S. Provisional Application No. 61/041,547, filed Apr. 1, 2008, the entire contents of which are hereby incorporated in its entirety for all purposes as if fully set forth herein.

BACKGROUND OF THE INVENTION

Field of the Invention

The field of the present invention is generally related to ophthalmic laser systems and more particularly, to apparatus, systems, and methods of iris-pupil contrast enhancement in ophthalmic laser surgery.

Background

In current ophthalmic laser surgery procedures, a combination of optical microscopes and directed light from a light source is used to view the patient's eye. These optical microscopes typically use refractive lenses to focus light into the viewer's eye or another light detector. More recently, image sensors, such as photoelectric light sensor arrays using charge coupled devices (CCDs) (e.g., complementary metal oxide semiconductor (CMOS) sensors), have been developed and capture digital images. When implemented as a digital camera, the digital camera can capture images of the patient's eye.

Centration or alignment of the laser and laser output with the patient's eye is typically a preliminary step for most ophthalmic laser surgery procedures. In general, centration or alignment with the patient's eye is accomplished using the image of the patient's eye and, to some extent, delineating the pupil from the iris. The light intensity or light source direction (e.g., in relation to the eye) may be modified to improve the overall brightness of the imaged eye including both the pupil and iris. Additionally, some displays have a general contrast control to vary the contrast of the entire displayed image to some degree. These techniques may be helpful to delineate the pupil from the iris for lighter eye colors (i.e., lighter iris color). When imaging the eye with a digital camera or other image sensor based device, delineating the pupil from the iris for darker-colored eyes (e.g., brown-colored eyes appear darker than blue-colored eyes) may be difficult and thus, interfere with centration or alignment using the resulting imaged patient's eye. For example, the difference in brightness between a brown-colored iris and a black-colored pupil is much less than the difference in brightness between a blue-colored iris and a black-colored pupil. Changing the light intensity or light source direction or adjusting conventional contrast controls on displays may not sufficiently differentiate the brightness between the brown-colored iris and the black-colored pupil. Additionally, conventional digital video cameras have relatively limited resolution. While images from these conventional digital video cameras may be magnified, the image detail decreased with magnification. Thus, the effective image magnification capabilities of conventional digital video cameras are limited (e.g., for delineating the pupil from the iris for darker-colored eyes).

Accordingly, it is desirable to provide an ophthalmic surgical system and a method of ophthalmic laser surgery that improves centration or alignment with the eye. It is also desirable to provide an ophthalmic surgical system and a method of ophthalmic laser surgery that selectively enhances the contrast of an imaged eye. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed towards photoaltering a region of an eye using an enhanced contrast between the iris and pupil of the imaged eye. In one embodiment, a system is provided including a laser assembly configured to output a pulsed laser beam, a user interface configured to display one of a first digital image of the eye and a second digital image of the eye, and a controller coupled to the laser assembly and the user interface. The first digital image has a first contrast between the pupil and the iris, and the second digital image has a second contrast between the pupil and the iris. The controller is configured to selectively increase the first contrast between the pupil and the iris to the second contrast between the pupil and the iris and direct the pulsed laser beam to the region of the eye based on one of the first and second digital images.

In another embodiment, a method is provided including producing a first digital image of the eye, selectively increasing a first contrast between the iris and the pupil to a second contrast between the iris and the pupil, displaying a second digital image of the eye, centrating the eye based on the second contrast, and directing a pulsed laser beam at the region. The first digital image has the first contrast between the iris and the pupil, and the second digital image has the second contrast.

In another embodiment, a computer system is provided including a processor, and a memory storing computer readable instructions that when executed by the processor cause the computer system to perform a method of photoaltering a region of an eye. The method includes producing a first digital image of the eye, selectively increasing a first contrast between the iris and the pupil to a second contrast, displaying a second digital image of the eye, centrating the eye based on the second contrast between the iris and the pupil, and directing the pulsed laser beam at the region. The first digital image has the first contrast between the iris and the pupil, and the second digital image has the second contrast.

BRIEF DESCRIPTION OF THE DRAWINGS

In the drawings, wherein like reference numerals refer to similar components.

DETAILED DESCRIPTION

The present invention generally provides systems and methods for photoaltering (e.g., using a laser) a desired region of the eye (e.g., a sub-surface region of the eye, such as within the corneal epithelium and on or within Bowman's layer, the stroma, Descemet's membrane, the endothelium, or the like) with an enhanced imaging component. Examples of photoalteration include, but are not necessarily limited to, chemical and physical alterations, chemical and physical breakdown, disintegration, ablation, vaporization, or the like. Using a digital image of the eye, an operator aligns and/or centrates the laser with the desired region prior to directing pulsed laser beams to the desired region. At times, the operator may desire an enhanced image of the eye than provided in the initial digital image. In one embodiment, the system increases the contrast between the iris and pupil displayed in the digital image of the eye in response to an operator selected function. For example, a dark/light eye function may be provided to the operator on a display, as a separate component of the system, or otherwise available for selection by the operator via an input device. For darker colored eyes, the operator can select the dark/light eye function to increase the contrast between the iris and pupil displayed in the digital image and thereby improve the appearance of the digital image for alignment and/or centration (e.g., using a graphical aid overlaying the digital image) of the eye.

Figure 1:
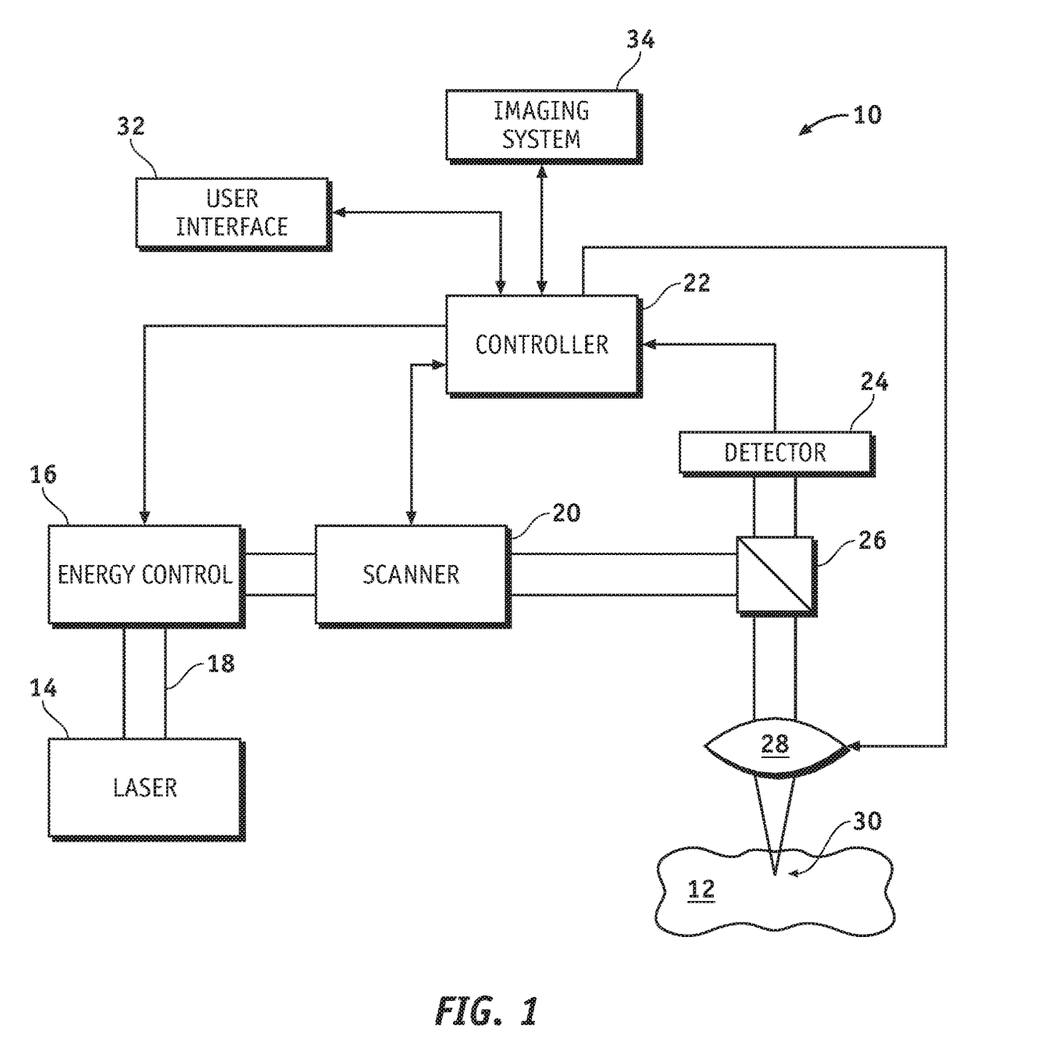
FIG. 1 is a block diagram of a system for photoaltering a region of an eye in accordance with one embodiment of the present invention.

Referring to the drawings, a system 10 for photoaltering a desired region 12 of an eye is shown in FIG. 1. The system 10 is suitable for ophthalmic applications but may be used to photoalter a variety of materials (e.g., organic, inorganic, or a combination thereof). In one embodiment, the system 10 includes, but is not necessarily limited to, a laser 14 capable of generating a pulsed laser beam 18, an energy control module 16 for varying the pulse energy of the pulsed laser beam 18, a scanner 20, a controller 22, a user interface 32, an imaging system 34, and focusing optics 28 for directing the pulsed laser beam 18 from the laser 14 on the surface of or within the region 12 (e.g., sub-surface). The controller 22 communicates with the scanner 20 and/or focusing optics 28 to direct a focal point 30 of the pulsed laser beam onto or into the material 12. To impart at least a portion of this control, software (e.g., instrument software, and the like), firmware, or the like, can be used to command the actions and placement of the scanner 20 via a motion control system, such as a closed-loop proportional integral derivative (PID) control system. In this embodiment, the system 10 further includes a beam splitter 26 and a detector 24 coupled to the controller 22 to provide a feedback control mechanism for the pulsed laser beam 18. The beam splitter 26 and detector 24 may be omitted in other embodiments, for example, with different control mechanisms.

One example of photoalteration using pulsed laser beams is the photodisruption (e.g., via laser induced optical breakdown). Localized photodisruptions can be placed at or below the surface of the material to produce high-precision material processing. For example, a micro-optics scanning system may be used to scan the pulsed laser beam to produce an incision in the material, create a flap of material, create a pocket within the material, form removable structures of the material, and the like. The term "scan" or "scanning" refers to the movement of the focal point of the pulsed laser beam along a desired path or in a desired pattern.

To provide the pulsed laser beam, the laser 14 may utilize a chirped pulse laser amplification system, such as described in U.S. Pat. No. RE37,585, for photoalteration. U.S. Pat. Publication No. 2004/0243111 also describes other methods of photoalteration. Other devices or systems may be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

The system 10 is capable of generating the pulsed laser beam 18 with physical characteristics similar to those of the laser beams generated by a laser system disclosed in U.S. Pat. Nos. 4,764,930, 5,993,438, or the like. For example, the system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue. The wavelength of the pulsed laser beam 18 is generally in the range of about 3 μm to about 1.9 nm, preferably between about 400 nm to about 3000 nm, and the irradiance of the pulsed laser beam 18 for accomplishing photodisruption of stromal tissues at the focal point is greater than the threshold for optical breakdown of the tissue. Although a non-UV, ultrashort pulsed laser beam is described in this embodiment, the laser 14 produces a laser beam with other pulse durations and different wavelengths in other embodiments.

In this embodiment, the focusing optics 28 direct the pulsed laser beam 18 toward the eye (e.g., onto the cornea) for plasma mediated (e.g., non-UV) photoablation of superficial tissue, or into the stroma for intrastromal photodisruption of tissue. The system 10 may also include an applanation lens (not shown) to flatten the cornea prior to scanning the pulsed laser beam 18 toward the eye. A curved, or non-planar, lens may substitute this applanation lens to contact the cornea in other embodiments.

The user interface 32 provides a flexible and simple environment for the operator to interact with the system 10. In one embodiment, the user interface 32 graphically displays (e.g., using a flat panel display or the like) information, such as from the instrument software controlling the operation of various components of the system 10, and provides a visual interface between the system 10 and the operator for inputting commands and data associated with the various components of the system. A graphical user interface (GUI) is preferably used with the user interface 32 employing menus, buttons, and other graphical representations that display a variety of selectable functions to be performed by the system 10 following selection. For example, the operator may point to an object and select the object by clicking on the object, touching a pre-designated region of a touch-screen displaying the GUI, or the like. Additional items may be presented on the GUI for operator selection, such as a button or menu item indicating an available sub-menu (e.g., a drop-down sub-menu). The user interface 32 may also utilize one or more of a variety of input devices including, but not necessarily limited to, a keyboard, a trackball, a mouse, a touch-pad, a touch-sensitive screen, a joystick, a variable focal length switch, a footswitch, and the like.

In addition to the user interface 32, the imaging system 34 displays a magnified real-time digital image of the patient's eye and provides an interface for viewing the patient's eye and operator control of the centration or alignment of the laser output with the patient's eye. In one embodiment, an alignment or centration aid is displayed by the imaging system 34 overlaying the digital image of the patient's eye. The aid corresponds with the position of laser output with reference to the patient's eye. As part of the photoalteration process, the output of the laser 14 is preferably aligned with the desired region 12 of the eye. For example, the output of the laser 14 may be substantially centered with reference to the pupil and iris of the patient's eye. Viewing the digital image displayed by the imaging system 34, the operator can center the aid based on the pupil and the iris of the patient's eye and thereby adjust the position of the laser output. To facilitate this alignment or centration process, the operator may desire a greater contrast between the iris and the pupil than shown in digital image of the patient's eye displayed by the imaging system 34.

In one embodiment, a user selectable dark/light eye function (e.g., represented as an icon, button, or the like) is provided (e.g., as a part of the imaging system 34, the user interface 32, or the system 10). When selected or activated (e.g., by touch), portions of the patient's eye that are normally darker in appearance in the digital image are displayed by the imaging system 34 with greater contrast (e.g., sufficient contrast to delineate each of the darker portions of the patient's eye. For example, for a brown iris and black pupil combination of a patient eye, the brown iris and black pupil are both relatively darker portions of the digitally imaged eye (e.g., in comparison with a lighter scleral portion of the digitally imaged eye). By selecting the dark/light eye function, the imaging system 34 displays a digital image of the patient's eye with greater contrast between the brown iris and the black pupil in the digital image, for example.

After alignment or centration, the system 10 directs the pulsed laser beam 18 to the desired region 12 of the eye. Movement of the focal point of the pulsed laser beam 18 is accomplished via the scanner 20 in response to the controller 22. The step rate at which the focal point is moved is referred to herein as the scan rate. For example, the scanner 20 can operate at scan rates between about 10 kHz and about 400 kHz, or at any other desired scan rate. In one embodiment, the scanner 20 generally moves the focal point of the pulsed laser beam 18 through the desired scan pattern at a substantially constant scan rate while maintaining a substantially constant separation between adjacent focal points of the pulsed laser beam 18. Further details of laser scanners are known in the art, such as described, for example, in U.S. Pat. No. 5,549,632, the entire disclosure of which is incorporated herein by reference.

In one embodiment, the scanner 20 utilizes a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point 30 of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

To create a flap, the pulsed laser beam 18 is typically scanned along in the desired region 12 using one or more patterns (e.g., a spiral pattern, a raster pattern, and the like) or combinations of patterns. When preparing a cornea for flap separation, for example, a circular area, oval area, or other shaped area may be scanned using a scan pattern driven by the scanning mirrors. The pulsed laser beam 18 photoalters the stromal tissue as the focal point 30 of the pulsed laser beam 18 is scanned along a corneal bed. The scan rates may be selected from a range between about 30 MHz and about 1 GHz with a pulse width in a range between about 300 picoseconds and about 10 femtoseconds, although other scan rates and pulse widths may be used.

The system 10 may additionally acquire detailed information about optical aberrations to be corrected, at least in part, using the system 10. Examples of such detailed information include, but are not necessarily limited to, the extent of the desired correction, and the location in the cornea of the eye associated with the correction (e.g., where the correction can be made most effectively). The refractive power of the cornea may be used to indicate corrections. Wavefront analysis techniques, made possible by devices such as a Hartmann-Shack type sensor (not shown), can be used to generate maps of corneal refractive power. Other wavefront analysis techniques and sensors may also be used. The maps of corneal refractive power, or similar refractive power information provided by other means, such as corneal topographs or the like, can then be used to identify and locate the optical aberrations of the cornea that require correction. The amount of photoalteration can be based on the refractive power map.

One example of an ophthalmic scanning application is a laser assisted in-situ keratomilieusis (LASIK) type procedure where a flap is cut from the cornea to establish extracorporeal access to the tissue that is to be photoaltered. The flap may be created using random scanning or one or more scan patterns. A sidecut is created around a desired perimeter of the flap such that the ends of the sidecut terminate, without intersection, to leave an uncut segment. This uncut segment serves as a hinge for the flap. The flap is separated from the underlying stromal tissue by scanning the laser focal point across a resection bed, the perimeter of which is approximately defined by the sidecut. In one embodiment, the perimeter of the resection bed is greater than the perimeter of the anterior surface of the flap to form a wedge-shaped flap edge. Once this access has been achieved, photoalteration is completed, and the residual fragments of the photoaltered tissue are removed from the cornea. In another embodiment, intrastromal tissue may be photoaltered by the system 10 so as to create an isolated lenticle of intrastromal tissue. The lenticle of tissue can then be removed from the cornea.

Figure 2:
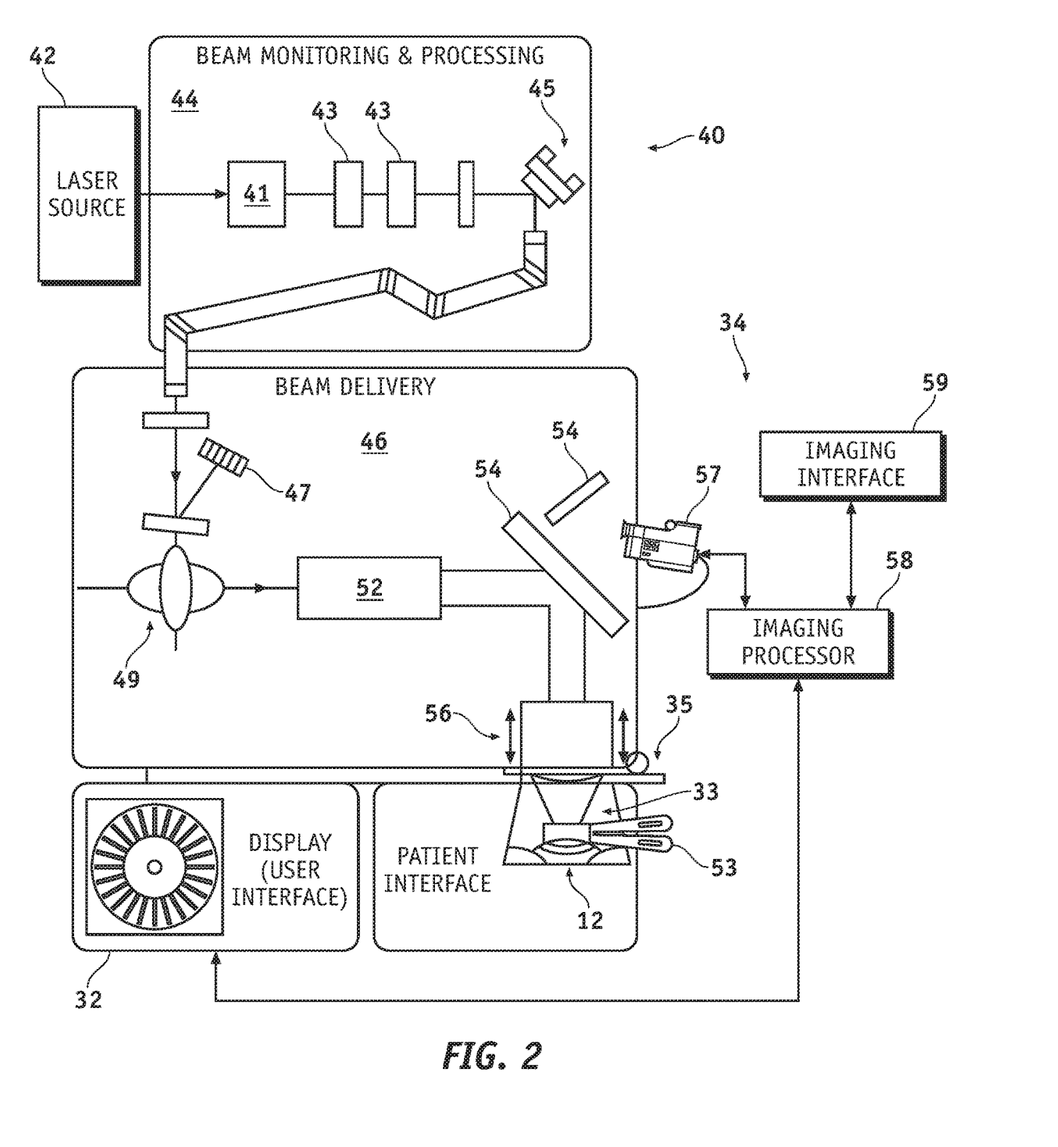
FIG. 2 is a block diagram of an ophthalmic laser system in accordance with one embodiment.

FIG. 2 is a block diagram of an ophthalmic laser system 40 in accordance with one embodiment of the present invention. Referring to FIGS. 1 and 2, the ophthalmic laser system 40 includes, but is not necessarily limited to, a laser source 42 providing a pulsed laser beam (e.g., the pulsed laser beam 18), a beam monitoring and processing module 44, a beam delivery module 46 coupled to the beam monitoring and processing module 44, the user interface 32, and the imaging system 34. The pulsed laser beam is supplied to the beam monitoring and processing module 44 where the pulse energy, the focal point separation, and optionally the minimum sub-surface depth of the pulsed laser beam are controlled. The beam delivery module 46 scans the pulsed laser beam along a desired scan region. In this embodiment, the ophthalmic laser system 40 can be coupled to an eye 31 via a patient interface 33, and the patient interface 33 may be coupled to the ophthalmic laser system 40 at a moveable loading deck 35, for example. The configuration of the ophthalmic laser system 40 may vary as well as the organization of the various components and/or sub-components of the ophthalmic laser system 40. For example, some components of the beam delivery module 46 may be incorporated with the beam monitoring and processing module 44 and vice versa.

The user interface 32 is coupled to the beam delivery module 45, and a variety of system parameters may be input or modified by the operator via the user interface 32 to control the beam properties and thus produce the desired photoalteration. For example, the user interface 32 may include a display presenting a graphical user interface with the various system parameters and an input device (not shown) for selecting or modifying one or more of these parameters. The number and type of system parameters vary for each type of ophthalmic procedure (e.g., flap creation, photorefractive keratectomy (PRK), LASIK, laser assisted sub-epithelium keratomileusis (LASEK), corneal pocket creation, corneal transplant, corneal implant, corneal onlay, and the like).

In one embodiment, the operating pulse energy and operating focal point separation of the pulsed laser beam may be input or selected by the operator via the user interface 48. For flap creation, the operator is prompted via the user interface 48 with a selection of flap pattern parameters (e.g., upper flap diameter, depth of incision in cornea, hinge angle, hinge position, and the like). The parameters may be displayed as default values for selective modification by the operator. Additional parameters may also be displayed by the user interface 48 for different procedures using the system 40. For example, a variety of pre-programmed ring pattern parameters (e.g., inner ring diameter, outer ring diameter, cornea thickness, incision axis, and the like) are provided for corneal ring implant procedures.

In response to the system parameters selected or input via the user interface 48, the beam monitoring and processing module 44 and/or the beam delivery module 46 produce a pulsed laser beam with the corresponding properties. In one embodiment, the beam monitoring and processing module 44 includes, but is not necessarily limited to, an energy attenuator 41, one or more energy monitors 43, and an active beam positioning mirror 45. The pulsed laser beam is directed from the laser source 42 to the energy attenuator 41, then to the energy monitor 43, and then to the active beam positioning mirror 45. The active beam positioning mirror 45 directs the pulsed laser beam from the beam monitoring and processing module 44 to the beam delivery module 46. Using the energy attenuator 41 and energy monitor 43, the pulse energy of the pulsed laser beam may be varied to desired values. Additionally, the spatial separation of the focal points of the pulsed laser beam may be varied by the beam monitoring and processing module 44.

The beam delivery module 46 scans the pulsed laser beam at the desired scan region (e.g., the region 12). In one embodiment, the beam delivery module 46 includes, but is not necessarily limited to, a beam position monitor 47, an x-y scanner 49, a beam expander 52, one or more beam splitters 54, and a z-scanning objective 56. The pulsed laser beam is received from the beam monitoring and processing module 44 by the x-y scanner 49 and directed to the beam expander 52, and the beam expander 52 directs the pulsed laser beam to the z-scanning objective via the beam splitter(s) 54. The z-scanning objective 56 can vary the focal point depth of the pulsed laser beam (e.g., from the anterior surface of the eye 31 or cornea to any depth within the eye 31 up to and including the retinal region).

Prior to initiating scanning or otherwise initiating photoalteration of the eye 31, the ophthalmic laser system 40 is coupled to the eye 31. In one embodiment, the patient interface 33 provides a surface for contacting the cornea of the patient's eye 31, which may also be used to applanate the cornea. A suction ring assembly 53 or other device may be applied to the eye 31 to fixate the eye prior to coupling the ophthalmic laser system 40 to the eye (e.g., via the patient interface 33). In one embodiment, the suction ring assembly 53 has an opening providing access to the eye 31 when coupled thereto. The imaging system 34 may be used to facilitate the coupling of the ophthalmic laser system 40 with the eye 31. For example, by providing a real-time image of the fixated eye, the operator can view the eye to properly center the output of the beam delivery module 46 over the desired region 12.

Once the ophthalmic laser system 40 is coupled to the eye 31, the imaging system 34 may be used for alignment or centration of the laser output (e.g., the beam delivery module 46 output) and/or applanation of the cornea using the patient interface 33. The imaging system 34 preferably provides a real-time, magnified, high resolution digital image of the eye 31 and includes, but is not necessarily limited to, an image sensor 57, an imaging interface 59, and an image processor 58 coupled to the sensor 57 and the interface 59. An image of the eye 31 is captured using the image sensor 57 and displayed by the imaging interface 59. In one embodiment, a high resolution digital camera (e.g., a high-definition digital video camera based on charge coupled devices (CCDs) or the like) is used to capture the image and display the image on the imaging interface 59.

Although FIG. 2 illustrates a combination of the image sensor 57 and beam splitters 54 for capturing the image, the image sensor 57 may be located in a variety of different positions or operate solely or operate with additional optical elements to directly or indirectly capture images of the eye 31. For example, the image sensor 57 may be located substantially adjacent to the z-scanning objective 56 to directly capture images of the eye 31. In one embodiment, the image sensor 57 is mounted on a moveable gantry to vary the image focal plane captured by the image sensor 57 and optically coupled with a variable aperture (not shown) (e.g., positioned between the image sensor 57 and the eye 31) for controlling the depth of focus and/or the amount of light sensed by the image sensor 57. In another embodiment, at least one or more of a focus control for varying the image focal plane captured by the image sensor 57 and a focus depth control are incorporated into the image sensor 57.

The imaging interface 59 includes, but is not necessarily limited to, an input device for operator selection of a variety of system parameters (e.g., associated with coupling the ophthalmic laser system 40 with the eye 31, image control, and the like) and a monitor displaying the real-time, magnified, high resolution digital image of the eye 31. The input device may include one or more of a keyboard, a trackball, a mouse, a touch-pad, a touch-sensitive screen, a joystick, a variable focal length switch, a footswitch, and the like. In one preferred embodiment, the imaging interface 59 includes a touch-sensitive screen displaying a graphical user interface for selecting the system parameters and for viewing the alignment or centration of the laser output with reference to the desired region 12 of the eye 31 and/or viewing the applanation of the cornea. The graphical user interface provides a variety of buttons, icons, or the like corresponding with different functions for selection by the operator, and the operator may select a particular function by touching the corresponding button displayed on the touch-sensitive screen. Examples of the different functions that may be provided by the graphical user interface at the imaging interface 59 include, but are not necessarily limited to, a dark/light eye function, an increase magnification function, a decrease magnification function, an increase illumination function, a decrease illumination function, an increase focal depth function, a decrease focal depth function, the functions and system parameters provided by the user interface 32, as previously described, and the like.

Operator control of the beam delivery module 46 alignment with the eye 31, applanation of the cornea, and/or centration may be provided via the input device of the imaging interface 59 or via a separate input device (e.g., a joystick). For example, the operator may control the raising, lowering, or lateral movement (two-dimensions) of the loading deck 35 via the joystick while viewing the digital image of the eye 31 provided by the imaging system 34. The operator can adjust the lateral position (e.g., an x-axis position and a y-axis position) of the loading deck 35 to align the output of the beam delivery module 46 with the eye 31 and lower the loading deck 35 (e.g., along a z-axis) to guide the patient interface 33 into a pre-determined position with the suction ring 53 (e.g., coupling the beam delivery module 46 with the eye 31). An indicator may be displayed by the imaging interface 59 (e.g., a green light) when the beam delivery module 46 is properly coupled with the eye 31 and/or when an applanation surface of the patient interface 33 contacts the cornea. The operator may then applanate the cornea by further lowering the beam delivery module 46 (e.g., the loading deck 35 and patient interface 33) using the input device, while monitoring the degree of applanation as indicated by the digital image of the eye 31, and discontinuing movement of the beam delivery module 46 at a desired degree of applanation determined by viewing the digital image of the eye 31.

In one embodiment, a centration aid is displayed as an overlay on the digital image of the eye 31 for assisting in centering the laser output with the desired region 12 of the eye 31 (e.g., to be photoaltered). The centration aid corresponds with the current position of the laser output with reference to the eye 31 (e.g., the two-dimensional position in the focal plane of the pulsed laser beam and/or axial alignment of the pulsed laser beam with reference to an optical axis of the eye 31). The operator may align or center the laser output using the joystick or other input device. For example, by centering the centration aid with reference to the image of the pupil, the iris, or both the pupil and iris, displayed by the imaging interface 59, the operator may adjust the output of the beam delivery module 46 to be centered with reference to the pupil, the iris, or both the pupil and iris. The centration aid may also be configured with reference to other anatomical indicators of the eye or other reference points. Following alignment or centration, the operator may initiate scanning and photoalteration of the desired region 12 of the eye 31.

The operator may continuously view the digital image of the eye 31 provided by the imaging system 34 during alignment or centration, applanation, the entire process from initial fixation of the eye through photoalteration of the eye, or any other portion of such process. For example, the physician performing the ophthalmic laser procedure may perform the ophthalmic laser procedure from fixation of the eye 31 (e.g., using the suction ring assembly 53), through coupling of the beam delivery module 46 to the eye 31 (e.g., via coupling of the patient interface 33 with the suction ring assembly 53), through applanation of the cornea, through centration, and through photoalteration of the desired region 12 of the eye 31, while maintaining viewing of the digital image of the eye 31 provided by the imaging system 58. The physician does not have to switch from viewing the imaging interface 59 to viewing the user interface 32 and/or does not have to switch from viewing the imaging interface 59 to directly viewing the patient's eye. Using the imaging system 34 simplifies and enhances the physician's focus on the ophthalmic laser procedure by allowing the physician to view a single display for an entire ophthalmic laser procedure.

At times, the operator may desire a greater contrast between the pupil and the iris shown in the digital image of the eye 31 captured by the imaging system 34. In general, the image sensor 57 captures an initial digital image of the eye 31 based on default settings. For example, in one embodiment, the image sensor 57 has a gamma function, which controls the intensity or brightness of each pixel of the digital image displayed by the imaging interface 59 based on the image detected by the image sensor 57. The typical default is a linear gamma function, and the image detected by the image sensor 57 is displayed by the imaging system 34 on the imaging interface 59 as with an intensity or brightness based on the linear gamma function.

As previously mentioned, a user-selectable button is provided at the imaging interface 59 for activating the dark/light eye function. When this function is selected (e.g., by touching a dark/light eye button on the touch-sensitive screen), the image processor 58 modifies the gamma function to a pre-determined setting (e.g., different from the default) and alters the intensity or brightness of the displayed image to enhance contrast between the lower intensity or lower brightness levels. This setting may be selected such that darker-colors detected by the image sensor 57 (e.g., brown eyes and black pupils) that are relatively close in intensity or brightness levels can be contrasted from one another to a greater degree than provided using the linear gamma function. For example, the image processor 58 retrieves a first set of intensity or brightness values (associated with the default gamma function setting) from a look-up table (not shown), which is used to produce the initial digital image of the eye 31. When the dark/light eye function is selected, the image processor 58 retrieves a second set of intensity or brightness values (associated with a non-linear or greater than linear gamma function setting) from the look-up table, which is used to produce an enhanced digital image of the eye 31 with greater contrast between the pupil and iris, particularly suited for darker-colored eyes.

The darker-colors detected by the image sensor 57 are thus displayed by the imaging interface 59 with a greater difference in relative intensity or brightness. In effect, selecting the dark/light eye function modifies the setting of the gamma function from the default setting to a setting that is more sensitive to the changes in intensity or brightness for darker-colored regions of the eye 31 as detected by the image sensor 57. For example a small change in intensity or brightness from one darker-color to another darker-color detected by the image sensor 57 produces corresponding pixels with a greater change in intensity or brightness (e.g., greater than a linear change, such as two-fold increase, a three-fold increase, a squared function, an exponential function, and the like). The enhanced digital image of the eye 31 provided by the dark/light eye function further assists the operator during centration, or any other portion of the ophthalmic laser procedure, and is particularly suited for darker-colored eyes. De-selecting the dark/light eye function (e.g., by touching the dark/light eye button again) returns the gamma function setting to the default gamma function setting (e.g., linear).

In one embodiment, the image processor 58 is additionally coupled to the user interface 32 to transmit the captured digital image of the eye 31 to the user interface 32. In this embodiment, the digital image of the eye 31 may also be displayed by the user interface 32. Other functions, such as control of the various system parameters, may be transferred to the imaging system 34. Similarly, functions provided by the imaging system 34, such as alignment or centration, may also be transferred to the user interface 32.

Figure 3:
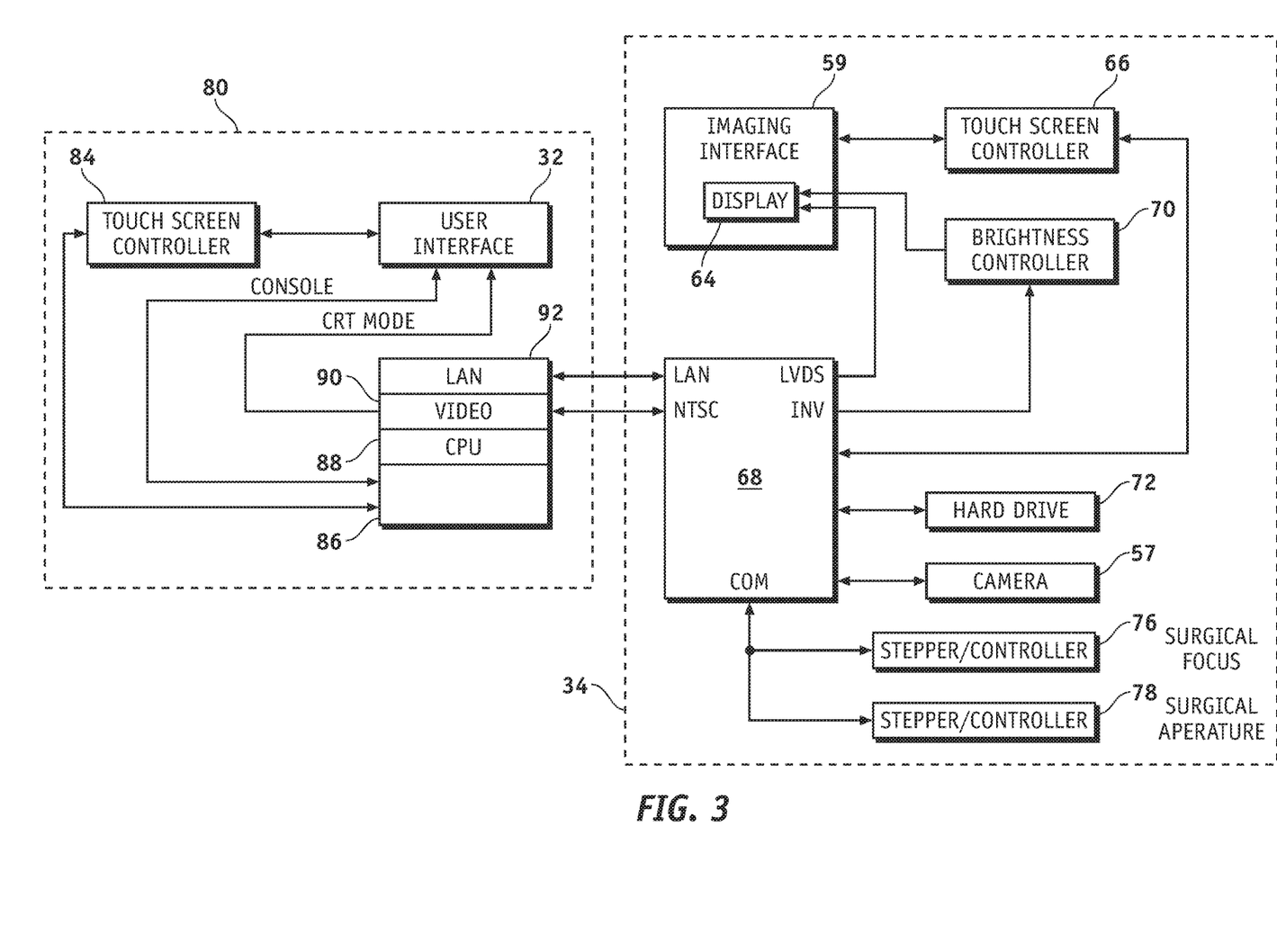
FIG. 3 is a block diagram of an interface system and the imaging system shown in FIGS. 1 and 2 in accordance with one embodiment of the present invention.

FIG. 3 is a block diagram of an interface system 80 and the imaging system 34 shown in FIGS. 1 and 2 in accordance with one embodiment of the present invention. In this embodiment, the interface system 80 includes, but is not necessarily limited to, the user interface 32 having a touch-sensitive screen, a touch screen controller 84 coupled to the user interface 32, and a central computing unit 86 coupled to the user interface 32 and the touch screen controller 84. The central computing unit 86 includes, but is not necessarily limited to, one or more communication ports (e.g., USB ports), a network component 92 (e.g., an Ethernet Gbit local area network (LAN) board), a video component 90 (e.g., a video board) coupled to the user interface 82 via a video input port (e.g., a cathode ray tube (CRT) mode input port), and a central processing unit (CPU) 88 (e.g., a CPU mother board). The central computing unit 86 is also coupled to the user interface 32 via one of the communication ports and to the touch screen controller 84 via another of the communication ports. The video component 90 receives a video signal (e.g., a National Television System Committee (NTSC) video signal) via an input port (e.g., an NTSC port) from the imaging system 34. Thus, the user interface 82 may operate with the central computing unit 86 as a console and may operate to display digital video received from the imaging system 34.

The imaging system 34 includes, but is not necessarily limited to, the imaging interface 59 having a display 64, a touch screen controller 66 coupled to the imaging interface 59, a brightness controller 70 coupled to the display 64, a processor 68 (e.g., a single board computer (SBC) with embedded board expandable (EBX) format and using a Pentium M 1.8 GHz microprocessor produced by Intel Corp.) coupled to the brightness controller (e.g., via an inverter port) and the touch screen controller, a data storage device 72 (e.g., a hard drive or the like) coupled to the processor 68, and the image sensor 57 coupled to the processor 68. The image sensor 57 is preferably a digital camera having a high resolution (e.g., 1624×1224 resolution) and more preferably has a resolution of about 2 megapixels or greater with a high frame rate (e.g., 1624× 1224 at about 20 frames per second or greater), such as the model GRAS-20S4M/C digital camera manufactured by Point Grey Research, Inc. The display 64 may have a resolution (e.g., 1024×768 resolution) that is less than the resolution of the digital camera. In these embodiments, the information captured by the high resolution digital camera is compressed by the processor 68 to the resolution of the display 64.

In this embodiment, the imaging interface 59 has a touch-sensitive screen and a graphical user interface is displayed on the display 64 by the processor 68. The processor 68 operates with the touch screen controller 66 and brightness controller 70 to control or modify the brightness level of the digital image of the eye when the dark/light eye button is selected. As previously described, the digital image of the eye captured by the image sensor 57 is displayed on the display 64 with an initial brightness level. For example, when the dark/light eye button is not selected, the processor 68 retrieves intensity or brightness data corresponding with the default setting from a look-up table stored in the data storage device 72.

The brightness level of the digital image may be modified when the dark/light eye button is selected. For example, the dark/light eye button may be displayed on the display 64 during operation of the graphical user interface by the processor 68. When the dark/light eye button is selected (e.g., detected by the touch screen controller 66), the touch screen controller 66 transmits a signal to the processor 68 indicating activation of the dark/light eye function. The processor 68 retrieves intensity or brightness data corresponding with the dark/light eye function from a look-up table stored in the data storage device 72 and instructs the brightness controller 70 to modify the digital image displayed on the display 64. In one embodiment, the dark/light eye function may have varying degrees of pre-determined contrast settings (e.g., corresponding with one or more of the different non-linear or greater than linear gamma functions), and the graphical user interface may be modified with a slide feature, successive button-tap feature, or the like, to provide operator selection of the different contrast settings.

The graphical user interface may also provide selectable buttons, icons, or the like for operator control of focus and/or magnification of the displayed digital image of the eye. A first stepper/controller 76 is coupled to the processor 68 to control the focus of the image sensor 57, and a second stepper/controller 78 is coupled to the processor 68 to control the aperature of the image sensor 57. By detection (e.g., via the touch screen controller 66) of a focus button (e.g., an increase focus button or a decrease focus button) selection or a magnification button (e.g., an increase magnification button or a decrease magnification button) selection, the processor 68 instructs the stepper/controller 76, 78, respectively.

In one embodiment, the data storage device 72 stores one or more applications (e.g., containing computer readable instructions) that when executed by the processor 68 cause the system 10, 40 to photoalter the desired region 12 of the eye 31. For example, the application, when executed, produces an initial digital image of the eye 31 having an initial contrast between the iris and the pupil, increases (e.g., from the initial contrast) the contrast between the iris and pupil upon operator selection of the dark/light eye function, displays a modified digital image of the eye 31 having the increased contrast the iris and pupil, centrates the eye 31 based on the increased contrast between the iris and pupil, and directs the pulsed laser beam at the desired region 12. When producing the initial digital image (e.g., without activation of the dark/light eye function), the processor 68 retrieves brightness data from the data storage device 72 that corresponds with a default setting (e.g., the default gamma function setting). To increase the contrast between the iris and pupil, the processor 68 retrieves brightness data from the data storage device 72 corresponding with a modified setting (e.g., the non-linear or greater than linear gamma function setting). The modified digital image is produced based on the brightness data corresponding with the modified setting.

The processor 68 is also coupled (e.g., with a LAN port) to the central computing unit 86 via a network, such as Ethernet and/or a GigaLAN, and information (e.g., selected system parameters, graphical user interface functions, and the like) may be transferred between the imaging system 34 and the interface system 80.

Figure 4:
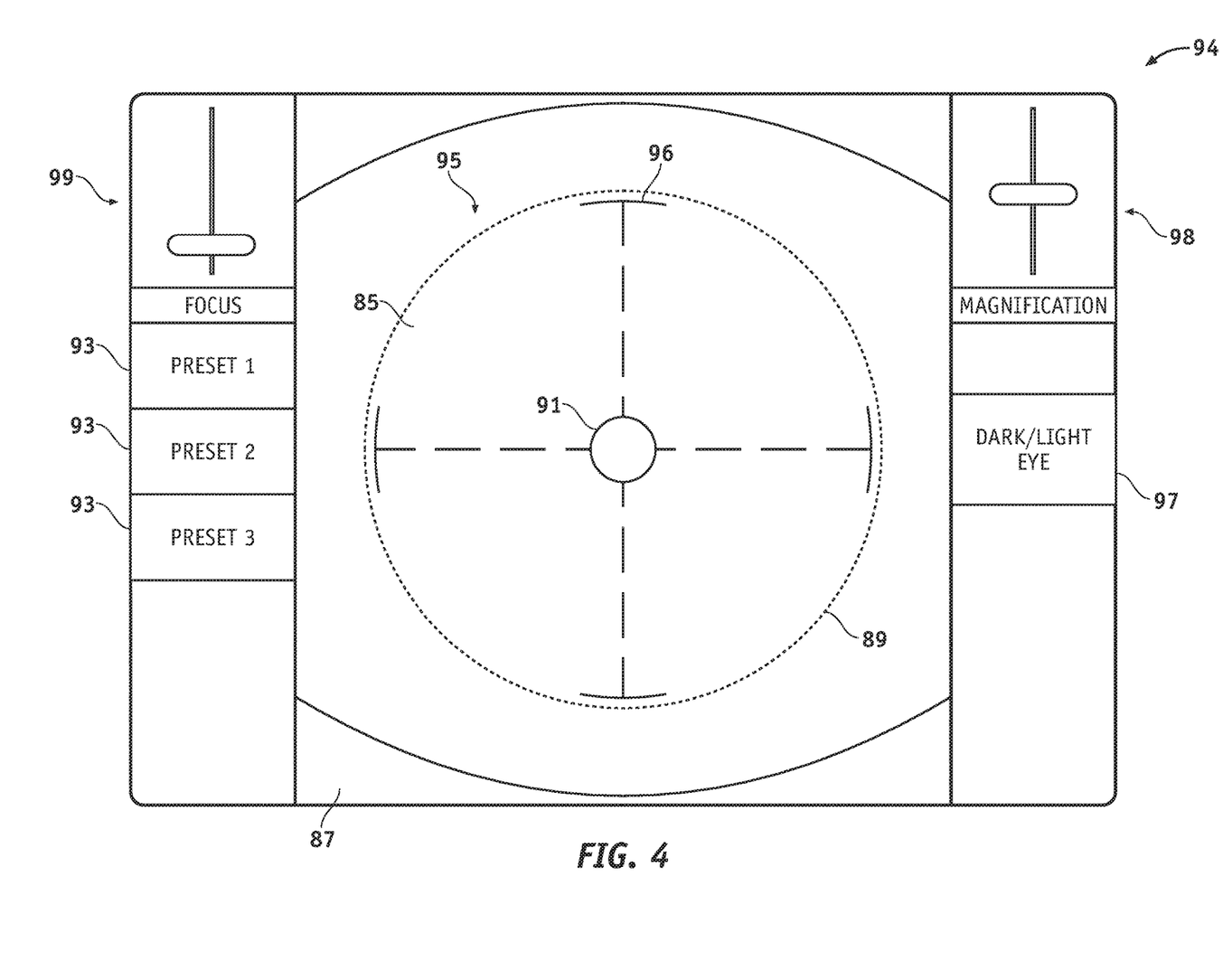
FIG. 4 is a front view of a graphical user interface in accordance with one embodiment.

FIG. 4 is a front view of a graphical user interface 94 in accordance with one embodiment. The graphical user interface 94 may be used with the imaging system 34 and/or the user interface 32 shown in FIGS. 1-3 to display a real-time, high resolution, digital image 95 of the patient's eye and provide a touch-sensitive screen for operator input. The graphical user interface 94 includes, but is not necessarily limited to, a focus control 99, a magnification control 98, preset focus depth buttons 93 (e.g., Preset 1, Preset 2, and Preset 3), a dark/light eye button 97, and a window 87 displaying the digital image 95 of the patient's eye. Additional buttons, icons, or the like may be provided by the graphical user interface 94. In this embodiment, a centration aid 96 is also displayed in the window 87 as an overlay on the digital image 95 of the eye. Each of the focus and magnification controls 99 and 98, respectively, is a sliding button representation that may be controlled by operator touch and/or touch and slide (e.g., up or down). During centration, the operator can touch the dark/light eye button 97 to enhance or increase the contrast between the pupil 97 and the iris 85 in the digital image 95. This enhanced or increased contrast improves the operator's ability to delineate between the pupil 85 and the iris 91 for centering the centration aid 96 (e.g., aligning the centration aid 96 with an outer boundary 89 of the iris 85). The centration aid 96 may have a variety of different configurations.

In another embodiment, one or more regions of the displayed digital image 95 of the eye may be selected to enhance the contrast therein. For example, a region for contrast enhancement may be selected by the operator using a stylus, pen, or other device to contact the touch-sensitive screen and/or circumscribe the desired region corresponding to the region of the displayed digital image 95 (e.g., within the window 87).

Figure 5:
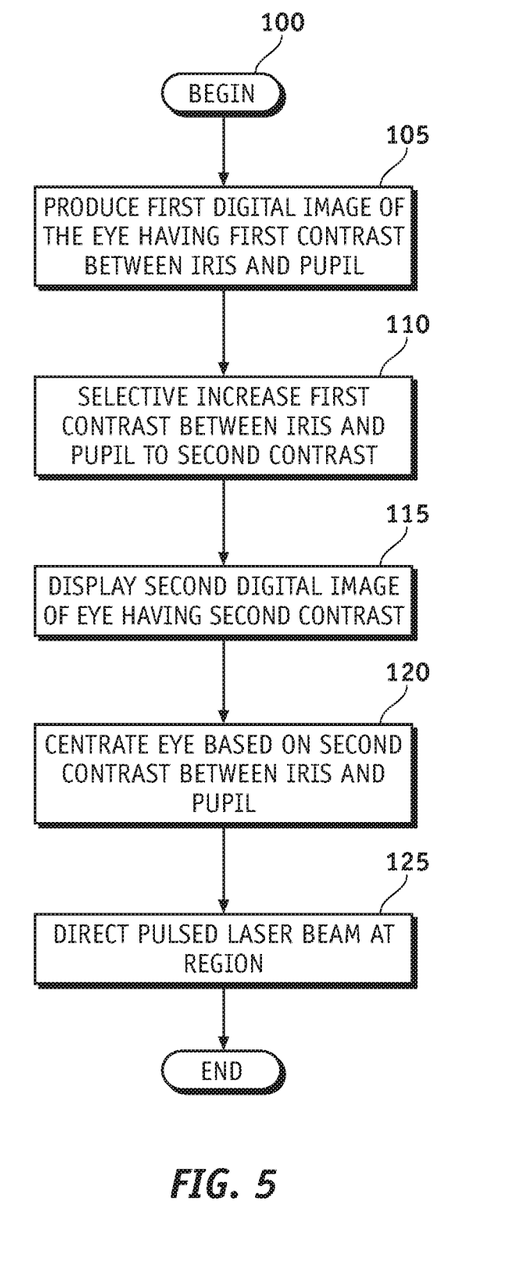
FIG. 5 is a flow diagram of a method for photoaltering a desired region of an eye in accordance with one embodiment.

FIG. 5 is a flow diagram of a method 100 for photoaltering a desired region of an eye using a pulsed laser beam in accordance with one embodiment. A first digital image of the eye is produced having an initial contrast between the iris and pupil, as indicated at step 105. For example, referring to FIGS. 1-4 and 5, an image of the eye 31 is captured with the image sensor 57 (e.g., a high resolution digital camera) and displayed using the graphical user interface 94 (e.g., in the window 87) by the imaging system 34 (e.g., via the display 64 of the imaging interface 59). The image sensor 57 has a default linear gamma function. In one embodiment, brightness data corresponding to the default linear gamma function and stored in a look-up table in the data storage device 72 is retrieved by the image processor 68 to produce the digital image of the eye 31 having the initial contrast (e.g., via the brightness controller 70) on the display 64. The initial contrast between the iris and pupil is based on the default linear gamma function. The contrast between the iris and pupil is selectively increased to a greater contrast, as indicated at step 110. In one embodiment, the contrast between the iris and pupil is increased upon operator selection (e.g., activating the dark/light eye function, which may be provided as a touchable button 97). For example, brightness data corresponding with a non-linear or greater than linear gamma function and stored in a look-up table in the data storage device 72 is retrieved by the image processor 68. This brightness data enhances or increases the contrast between the iris and pupil in the digital image of the eye and thus produces a digital image of the eye with enhanced or increased contrast (e.g., via the brightness controller 70 as instructed by the image processor 68). A second digital image of the eye is displayed (e.g., via the display 64 of the imaging interface 59) having the greater contrast, as indicated at step 115. The eye is centrated by the operator based on this greater contrast between the iris and pupil, as indicated at step 120. The pulsed laser beam is directed at the desired region, as indicated at step 125.

Thus, systems 10, 40 and method 100 of photoaltering a desired region of the eye are provided that selectively enhances or increases the contrast between the iris and pupil displayed by the imaging system 34. Examples of some refractive eye surgery applications for the systems 10, 40 and/or method 100 include, but are not necessarily limited to, photorefractive keratectomy (PRK), LASIK, laser assisted sub-epithelium keratomileusis (LASEK), or the like. Using the imaging system 34 of the systems 10, 40 and method 100 enhances contrast and facilitates operator centration or alignment of the laser output with the patient's eye (e.g., in the desired region of photoalteration).

While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A system comprising:
    a processor;
    a user input device; and
    a memory storing computer readable instructions that when executed by the processor cause the system to perform a method of photoaltering a region of an eye having an iris and a pupil, comprising:
        producing a first digital image of the eye, the first digital image having a first contrast between the iris and the pupil;
        in response to a first user input received via the user input device, displaying the first digital image of the eye;
        in response to a second user input received via the user input device, the second user input being different from the first user input, selectively increasing the first contrast between the iris and the pupil to a second contrast which is greater than the first contrast between the iris and the pupil;
        displaying a second digital image of the eye, the second digital image having the second contrast between the iris and the pupil;
        centrating the eye to align the eye with a pulsed laser beam based on the second contrast between the iris and the pupil; and
        after centrating the eye, directing the pulsed laser beam to the region of the eye to photoalter the region of the eye.

2. A system according to claim 1, wherein selectively increasing the first contrast comprises:
    retrieving brightness data from the memory, the second contrast based on the brightness data; and
    generating the second digital image from the brightness data.

3. A system according to claim 1, wherein producing the first digital image comprises retrieving first brightness data from the memory, the first brightness data based on a linear relationship, the first digital image based on the first brightness data; and wherein selectively increasing the first contrast comprises:

retrieving second brightness data from the memory, the second brightness data based on a non-linear relationship, the second contrast based on the second brightness data; and generating the second digital image from the second brightness data.

4. The system of claim 1, further comprising:
an imaging interface;
a data storage device; and
a digital camera having an image sensor,
wherein producing the first digital image of the eye comprises capturing an image of the eye with the digital camera, the digital camera having a gamma function setting which converts a brightness of portions of the image captured by the image sensor to a brightness of each pixel displayed on the imaging interface, wherein the first digital image having the first contrast is produced based on the gamma function setting of the digital camera which is set to a linear default gamma function setting,
wherein the user input is a user-selectable button; and
wherein the method of photoaltering further comprises in response to a user manually activating the user-selectable button in response to the eye being a brown eye, increasing the first contrast between the iris and the pupil to the second contrast by modifying the digital camera's gamma function from the linear default setting to a non-linear function that enhances contrast of the pixels displayed on the imaging interface between the pupil and darker colored irises, wherein the non-linear function increases the contrast of the pixels displayed on the imaging interface between the pupil and darker colored irises based on values in a look-up table stored in the data storage device.

5. The system of claim 1, further comprising a user interface, wherein the user interface is further configured to display a centration aide overlaying the second digital image of the eye; and wherein the method further comprises:

positioning the centration aide into an alignment with respect to the pupil and the iris in response to a second user input; and directing the pulsed laser beam to the region of the eye in alignment with the centration aide.

6. The system of claim 5, wherein the user input device comprises a touch-sensitive screen coupled with the user interface.

7. The system of claim 1, further comprising a sensor coupled to the processor, the sensor configured to capture image data and transmit the image data to the processor; and wherein:

the step of producing the first digital image of the eye includes selecting first brightness data corresponding with the image data, the first contrast based on the first brightness data; and the step of selectively increasing the first contrast to the second contrast includes selecting second brightness data corresponding with the image data, the second contrast based on the second brightness data.

8. The system of claim 7, wherein the memory is configured to store a look-up table of a pre-determined first correspondence between a set of input values and a first set of output values and a pre-determined second correspondence between the set of input values and a second set of output values;

wherein the selecting of the first brightness data includes using the image data as input values for the look-up table to retrieve corresponding first output values as the first brightness data; and wherein the selecting of the second brightness data includes using the image data as input values for the look-up table to retrieve corresponding second output values as the second brightness data.

9. The system of claim 7, wherein the first brightness data corresponds to a linear brightness function, and wherein the second brightness data corresponds to a non-linear brightness function.

10. The system of claim 1, wherein the user input device comprises a voice recognition device.

11. The system of claim 1, wherein the user input device comprises a user-selectable button configured for a user to either generate the second user input which indicates that the iris of the eye is brown, or to generate the first user input which indicates that the iris of the eye is a different color than brown.

12. A system for photoaltering a region of the eye having an iris and a pupil, comprising:

a laser assembly configured to output a pulsed laser beam;
a processor;
a user interface, the user interface including a user input device configured for a user to indicate that the iris is brown; and
a memory storing computer readable instructions that when executed by the processor cause the system to perform a method of photoaltering the region of the eye by:

producing a first image of the eye, wherein the first image is produced using a first gamma function which provides a first contrast between the iris and the pupil;

displaying the first image of the eye on the user interface;

in response a user input provided via the user input device, producing a signal indicating that the iris of the eye is brown;

in response to the signal indicating that the iris of the eye is brown, producing a second image of the eye, wherein the second image is produced using a second gamma function which provides a second contrast between the iris and the pupil which is greater than the first contrast provided by the first gamma function;

displaying the second image of the eye on the user interface;

centrating the eye to align the pulsed laser beam with the eye based on the second contrast between the iris and the pupil provided by the second gamma function; and directing the pulsed laser beam to the region of the eye to photoalter the region of the eye.

13. The system of claim 12, wherein the user interface is further configured to display a centration aide overlaying the second image of the eye; and wherein the computer readable instructions when executed by the processor cause the system to:

position the centration aide into an alignment with respect to the pupil and the iris in response to a second user input; and direct the pulsed laser beam to the region of the eye in alignment with the centration aide.

14. The system of claim 13, wherein the user interface comprises a touch-sensitive screen and the user input device button displayed on the touch-sensitive screen.

15. The system of claim 12, further comprising a sensor coupled to the processor, the sensor configured to capture image data and transmit the image data to the processor; and wherein:
   the step of producing the first image includes selecting first brightness data corresponding with the image data, the first brightness data being associated with the first gamma function, the first contrast based on the first brightness data; and
   the step of producing the second image includes selecting second brightness data corresponding with the image data, the second brightness data being associated with the second gamma function, the second contrast based on the second brightness data.

16. The system of claim 15, wherein the memory is further configured to store a look-up table of a pre-determined first correspondence between a set of input values and a first set of output values and a pre-determined second correspondence between the set of input values and a second set of output values;
   wherein the selecting of the first brightness data includes using the image data as input values for the look-up table to retrieve corresponding first output values as the first brightness data; and
   wherein the selecting of the second brightness data includes using the image data as input values for the look-up table to retrieve corresponding second output values as the second brightness data.

17. The system of claim 12, wherein the user input device comprises a voice recognition device.

18. The system of claim 12, wherein the user input device comprises a user-selectable button configured for the user to indicate whether the iris of the eye: (1) is brown, or (2) is a different color than brown.

* * * * *